United States Patent [19]
Thomas et al.

[11] Patent Number: 6,008,419
[45] Date of Patent: *Dec. 28, 1999

[54] PROCESS FOR MAKING 2,3-DIHALOPROPANOLS

[75] Inventors: P. J. Thomas, Midland; R. Garth Pews, Stanwood; Paul C. Vosejpka; George J. Frycek, both of Midland, all of Mich.

[73] Assignee: The Dow Chemical Company, Midland, Mich.

[*] Notice: This patent is subject to a terminal disclaimer.

[21] Appl. No.: 08/994,208

[22] Filed: Dec. 19, 1997

Related U.S. Application Data

[63] Continuation-in-part of application No. 08/667,526, Jun. 19, 1996, Pat. No. 5,744,655.

[51] Int. Cl.$^6$ .................................................... C07C 29/38
[52] U.S. Cl. ........................ 568/862; 568/841; 568/881; 502/326
[58] Field of Search .................................. 568/840, 841, 568/842, 876, 878, 880, 881, 885, 861, 862; 502/326

[56] References Cited

U.S. PATENT DOCUMENTS

| | | | |
|---|---|---|---|
| 2,860,146 | 11/1958 | Furman et al. | 260/348.6 |
| 3,277,187 | 10/1966 | Dewhirst | 260/633 |
| 3,454,644 | 7/1969 | Dewhirst | 260/570.9 |
| 3,935,284 | 1/1976 | Kruse | 260/635 C |
| 4,024,193 | 5/1977 | Kruse | 260/618 D |
| 4,049,577 | 9/1977 | Childress et al. | 252/443 |
| 4,072,720 | 2/1978 | Haag et al. | 260/618 H |
| 4,088,281 | 2/1977 | Knowles et al. | 260/606.5 P |
| 4,129,600 | 12/1978 | Childress et al. | 260/604 R |
| 4,166,808 | 9/1979 | Daumas et al. | 252/455 R |
| 4,182,721 | 1/1980 | De Thomas et al. | 260/347.8 |
| 4,251,672 | 2/1981 | Carter et al. | 568/814 |
| 4,268,454 | 5/1981 | Pez et al. | 260/439 R |
| 4,273,939 | 6/1981 | Barnett et al. | 564/358 |
| 4,418,227 | 11/1983 | Pez et al. | 568/861 |
| 4,459,419 | 7/1984 | Seemuth | 549/429 |
| 4,503,249 | 3/1985 | Nowack et al. | 564/385 |
| 4,613,707 | 9/1986 | Kouba et al. | 568/864 |
| 4,626,604 | 12/1986 | Hiles et al. | 568/881 |
| 4,709,105 | 11/1987 | Grenacher et al. | 568/883 |
| 4,762,817 | 8/1988 | Logsdon et al. | 502/329 |
| 4,777,302 | 10/1988 | Haji et al. | 568/862 |
| 4,837,368 | 6/1989 | Gustafson et al. | 568/881 |
| 5,004,844 | 4/1991 | Van Leeuwen et al. | 568/880 |
| 5,093,535 | 3/1992 | Harrison et al. | 568/881 |
| 5,142,067 | 8/1992 | Wegman et al. | 549/326 |
| 5,155,086 | 10/1992 | Thakur et al. | 502/342 |
| 5,214,220 | 5/1993 | Drent | 568/881 |
| 5,225,389 | 7/1993 | Caillod et al. | 502/205 |
| 5,243,095 | 9/1993 | Roberts et al. | 568/864 |
| 5,326,916 | 7/1994 | Kobayashi et al. | 568/492 |
| 5,345,005 | 9/1994 | Thakur et al. | 568/885 |
| 5,550,302 | 8/1996 | Mori et al. | 568/881 |

FOREIGN PATENT DOCUMENTS

| | | |
|---|---|---|
| 630238 | 11/1991 | Australia . |
| 64-50834 | 2/1989 | Japan . |
| 64-52732 | 2/1989 | Japan . |

OTHER PUBLICATIONS

"Hydrogenation of aldehyde(s) and ketone(s)—over platinum gp. catalyst and methanol as hydrogen donor", Derwent 85–196564, Aug. 1, 1985.

"Hydrogenation of carbonyl cpds.—using ruthenium catalyst prepd. by impregnating ruthenium cpd. into organic oxide carrier, fixing with alkali then reducing", Derwent 91–078699, Feb. 5, 1991.

"Prepn. of chlorohydrin derivs.—by reaction of chloro–acetaldehyde with Grignard reagent", Derwent 96–065449, Dec. 12, 1995.

"Hydrogenation of carbonyl cpds. using ruthenium catalyst—obtd. by supporting ruthenium halide(s) on silica e.g. fixing with alkali and reducing", Derwent 90–379467, Nov. 8, 1990.

"Alcohol prodn. by catalytic aldehyde hydrogenation—comprises using monolith catalyst e.g. wash coated metal support impregnated with a noble metal", Derwent 95–367305, Oct. 26, 1995.

Abstract for JP Patent 57136533, Aug. 23, 1982.

R.A. Sanchez–Delgado et al., "Homogeneous Hydrogenation of Aldehydes to Alcohols with Ruthenium Catalysts", Journal of Organometallic Chemistry, vol. 209, No. 1, pp. 77–83 (1981).

*Primary Examiner*—Gary Geist
*Assistant Examiner*—Sreeni Padmanabhan

[57] ABSTRACT

A 2,3-dihalopropanol is made by reacting 2,3-dihalopropanal with molecular hydrogen in the presence of a transition metal-containing catalyst, under conditions such that 2,3-dihalopropanol is formed. The reaction is particularly useful, for example, as Step (3) in a process to make epihalohydrin which may be generally prepared by:

(1) reacting a 3-carbon hydrocarbon with an oxidizing agent to form acrolein;
(2) reacting acrolein with a molecular halogen to form 2,3-dihalopropanal;
(3) reducing 2,3-dihalopropanal with molecular hydrogen to form 2,3-dihalopropanol; and
(4) cyclizing 2,3-dihalopropanol to make epihalohydrin.

The process produces epihalohydrin using only about one mole of halogen per mole of epihalohydrin. It also uses substantially less water than existing processes.

48 Claims, No Drawings

PROCESS FOR MAKING 2,3-DIHALOPROPANOLS

This application is a CIP of 08/667,526 filed Jun. 19, 1996, now U.S. Pat. No. 5,744,655.

BACKGROUND OF THE INVENTION

The present invention relates to making 2,3-dihalopropanols.

2,3-Dihalopropanols are usually represented by:

Formula I
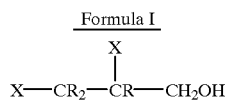

wherein:
each "X" is independently a halogen atom; and
each "R" is independently a hydrogen atom or an organic group. 2,3-Dichloropropanol is the most commonly used member of the class.

2,3-Dihalopropanols are important intermediates in the manufacture of epihalohydrin. For instance, epichlorohydrin is usually made by a three-step process of:
(1) reacting propylene and chlorine to make allyl chloride;
(2) reacting allyl chloride with hypochlorous acid to make a mixture of dichloropropanols; and
(3) reacting the dichloropropanols with a strong base to make epichlorohydrin.
This process makes large quantities of halogen-containing waste. For each mole of epichlorohydrin which is produced, at least about two moles of molecular chlorine are required. Each molecule of epichlorohydrin contains one atom of chlorine, and the remaining three atoms of chlorine are lost in the waste stream.

It has been proposed to make epihalohydrins by processes which are more efficient in their use of halogen. For instance, Furman et al. (U.S. Pat. No. 2,860,146 (Nov. 11, 1958)) proposed to make epihalohydrin by a three-step process of:
(1) reacting acrolein with chlorine to form 2,3-dichloropropanal;
(2) reacting 2,3-dichloropropanal with a secondary alcohol in the presence of a catalyst to form 2,3-dichloropropanol (transfer hydrogenation); and
(3) dehydrochlorinating 2,3-dichloropropanol to make epichlorohydrin.
However, the costs associated with this process are too high for it to be economically feasible, due to the cost of recycling coproduct ketone back to alcohol and regenerating catalyst. Furthermore, Furman et al. teaches that "ordinary methods of catalytic hydrogenation cannot be used successfully for the reduction step of the new process because of the poor yields and for high consumption of catalyst in the reaction."

What is needed is an economical process to make dihalopropanols with reduced production of halogenated waste.

SUMMARY OF THE INVENTION

One aspect of the present invention is a process to make 2,3-dihalopropanol comprising the step of reacting 2,3-dihalopropanal with a hydrogenating agent in the presence of a transition metal-containing catalyst, under conditions such that 2,3-dihalopropanol is formed.

A second aspect of the present invention is a process to make epihalohydrin comprising the steps of:

(1) reducing 2,3-dihalopropanal to form 2,3-dihalopropanol as described in the first aspect of the invention; and
(2) cyclizing 2,3-dihalopropanol to make epihalohydrin.

The process in the second aspect of the invention produces epihalohydrin using only about one mole of molecular halogen per mole of epihalohydrin. This process reduces the amount of halogenated organics in the waste stream by more than 60 percent, relative to the commercial allyl chloride route. The process also uses substantially less water than existing processes. The reducing agent may be hydrogen, so that there is no need to recycle ketone to alcohol, as in transfer hydrogenation.

DETAILED DESCRIPTION OF THE INVENTION

The present invention makes 2,3-dihalopropanol from a 2,3-dihalopropanal. 2,3-Dihalopropanal preferably is represented by:

Formula II
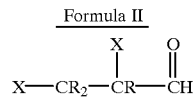

wherein:
each "X" is independently a halogen, is preferably chlorine or bromine and is most preferably chlorine; and
each "R" is independently hydrogen or a lower ($C_1$ to $C_6$) hydrocarbyl group, is preferably hydrogen or a lower alkyl group, is more preferably hydrogen or a methyl group and is most preferably hydrogen.

Examples of suitable 2,3-dihalopropanals useful in the present invention include: 2,3-dichloropropanal; 2,3-dibromopropanal; 2,3-dichloro-2-methylpropanal, 2,3-dibromo-2-methylpropanal and mixtures thereof. The 2,3-dihalopropanal used in the present invention is most preferably an unsubstituted 2,3-dichloropropanal to form 2,3-dichloropropanol. An unsubstituted 2,3-dibromopropanal can also be used to form 2,3-dibromopropanol.

The dihalopropanal is hydrogenated by reaction with a hydrogenating agent. The hydrogenating agent useful in the present invention may be, for example, molecular hydrogen, alcohols, or combinations thereof. The hydrogenating agent is preferably molecular hydrogen. Examples of suitable alcohols useful in the present invention can be primary or secondary alcohols such as methanol, ethanol and $C_3$—$C_{10}$ primary and secondary alcohols. Preferably, the alcohol is methanol. Examples of other secondary alcohols useful in the present invention are described in U.S. Pat. No. 2,860,146 incorporated herein by reference.

The reaction consumes one mole of hydrogenating agent per mole of dihalopropanol which is made. Generally, at least about 0.6 moles of hydrogenating agent per mole of 2,3-dihalopropanal are available to be consumed during the course of the reaction, preferably at least about 0.75 moles of molecular hydrogen per mole of 2,3-dihalopropanal are available to be consumed during the course of the reaction, more preferably at least about 0.9 moles and most preferably at least about 1 mole are available to be consumed during the course of the reaction. When less than 1 mole of hydrogenating agent per mole of 2,3-dihalopropanal is available to be consumed during the course of the reaction, the reaction is less efficient because complete conversion of the 2,3-dihalopropanal is not obtained. However, not all of the hydrogenating agent need be available at the start of the reaction. The hydrogenating agent may be added step-wise or continuously as the reaction progresses. In this case, the reaction mixture at any one time may contain a stoichiometric excess of dihalopropanal over hydrogenating agent. As one embodiment of the present invention, an excess of hydrogenating agent required may be used for completing the conversion in the reaction. Generally, for example, from 10 percent to 20 percent excess hydrogenating agent may be used.

The maximum quantity of hydrogenating agent source is not critical and is governed by practical considerations such as pressure, reactor efficiency and safety. When the hydrogenating agent source is gaseous, then the quantity of hydrogenating agent is preferably at least enough to provide the desired pressure. However, in most cases, the reactor preferably contains no more than about 1,000 moles of molecular hydrogen per mole of 2,3-dihalopropanal and more preferably contains no more than about 100 moles. Gaseous hydrogenating agent sources, such as molecular hydrogen, are preferably used according to known methods for mixing a gaseous reagent with a liquid reaction mixture, such as bubbling the gas through the mixture with agitation or solubilizing the hydrogen under pressure.

The reaction of the present invention takes place in the presence of a transition metal-containing catalyst. By transition metal, we mean a metal selected from any of Groups IB, IIB or IIIA–VIIIA on the periodic table of elements, as currently adopted by the International Union of Pure and Applied Chemistry (IUPAC), which is incorporated herein by reference. The catalyst metal useful in the present invention is selected such that under reaction conditions it catalyzes the hydrogenation of substantially all of the aldehyde moieties on the dihalopropanal molecule to primary alcohol moieties without substantially affecting the halogens which are bonded to the molecule. The catalyst metal is preferably selected from Group VIIIA of the periodic table, for example: iron, cobalt, nickel, ruthenium, rhodium, palladium, osmium, iridium, platinum and mixtures thereof. The catalyst metal is more preferably ruthenium, iridium, palladium or platinum and is most preferably ruthenium, iridium or combinations thereof.

The transition metal-containing catalyst useful in the present invention may be in homogeneous or heterogeneous form. The transition metal in the catalyst may be in an oxidized or unoxidized state.

A homogeneous catalyst useful in the reaction mixture of the present invention contains a soluble transition metal compound or complex. Examples of soluble transition metal compounds include metal halides, acetates hydroxides and mixtures thereof. The homogeneous catalyst useful in the present invention includes, for example, $RuCl_3$, $IrCl_3$, $RhCl_3$, $Rh_2(OAc)_4$, $PtCl_2$, $PdCl_2$, $Pd(OAc)_2$ and mixtures thereof.

Homogeneous catalysts preferably further contain a coordinating ligand. Examples of suitable coordinating ligands include phosphines, 1,5-cyclooctadiene (COD), norbornadiene (NBD), arsines, stibines, carbon monoxide, ethers, cyclopentadienyl (Cp), aromatic amines, sulfoxides such as dimethyl sulfoxide (DMSO) and mixtures thereof. Examples of suitable phosphines include, in particular, triaryl phosphine and more particularly triphenyl phosphine. Specific examples of the homogeneous catalysts useful in the present invention include $RuCl_2(PPh_3)_3$, $(COD)Ir(PPh_2Me)_2{}^+PF_6{}^-$, $RuHCl(PPh_3)_2(NBD)$, $RuHCl(CO)(PPh_3)_3$, $CpRuCl(PPh_3)_2$, $RuCl_2(PPh_3)_2[2-(COCH_3)C_5H_4N]$ and $RuCl_2(DMSO)_4$. Other homogeneous catalysts useful in the present invention may be found in the following references:

G. E. Coates et al., *Principles of Organometallic Chemistry*, Methven & Co. Ltd, London, 1971;

Charles M. Lukehart, *Fundamental Transition Metal Organometallic Chemistry*, Brooks/Cole Publishing Co., Monterey, Calif., 1985; George W. Parshall, *Homogenous Catalysis*, John Wiley & Sons, New York, 1980;

B. J. Huberoff, *Homogeneous Catalysis Industrial Applications and Implications*, American Chemical Society, Washington, D.C. 1968; and Brian R. James, *Homogeneous Hydrogenation*, John Wiley & Sons, New York, 1973; all incorporated herein by reference.

A homogeneous catalyst useful in the reaction mixture of the present invention may consist of a mixture of a soluble transition metal compound or complex with a coordinating ligand. Examples of such mixtures include $RuCl_3/PPh_3$, $RuCl_3/P(p-tol)_3$, $RuCl_3/P(C_6H_4-p-Cl)_3$, $IrCl_3/PPh_3$, $RhCl_3/PPh_3$.

The optimum number of coordinating ligands coordinated to the catalyst metal varies, depending upon the catalyst metal, the ligand, and the desired activity of the catalyst in a manner which is familiar to persons of ordinary skill in the art. It can readily be determined without undue experimentation. For example, when the transition metal is ruthenium and the ligand is a phosphine, the coordinated molar quantity of ligand per mole of metal is generally from about 0 to about 6 and preferably from about 2 to about 4. Preferably, the coordinated molar quantity of ligand per mole of metal is at least about 1 and preferably at least about 2. The coordinated molar quantity ratio is preferably no more than about 7, more preferably no more than about 6 and most preferably no more than about 4.

The preferred concentration of homogeneous catalyst varies widely depending upon the catalyst selected and its activity. For most homogeneous catalysts, the reaction mixture preferably contains at least about 0.01 mmoles of catalyst metal per mole of dihalopropanal, more preferably at least about 1 mmole and most preferably at least about 4 mmoles. The maximum concentration of homogeneous catalyst is not critical and is limited primarily by practical limits, such as cost. Usually, the catalyst metal concentration is preferably no more than about 100 mmoles per mole of dihalopropanal, more preferably no more than about 25 mmoles and most preferably no more than about 10 mmoles.

The heterogeneous catalysts useful in the present invention may be, for example, a transition metal deposited or absorbed on an insoluble support such as carbon, silica, alumina, zirconia, titania and other common supports known in the art as described in Poncelet et al. editors, *Preparation of Catalysts III*, New York, 1983; P. N. Rylander, *Hydrogenation Methods*, Academic Press, London, 1985; P. N. Rylander, *Catalytic Hydrogenation Over Platinum Metals*, Academic Press, New York, 1967; P. Rylander, *Catalytic Hydrogenation in Organic Syntheses*, Academic Press, New York, 1979 incorporated herein by reference; or the catalyst may be a transition metal coordinated to ligands bonded to a resin, for example ruthenium on phosphinated polystyrene.

For heterogeneous catalysts, the ideal ratio of catalyst to reagents varies depending upon flow rate, bed size, temperature, desired conversion, reagents and other factors. Usually, a heterogeneous catalyst bed contains about 0.0001 to about 100 moles of catalyst metal for each mole of dihalopropanal which passes through the bed per hour.

The reaction of the present invention is optionally, but preferably carried out in the presence of a protic solvent. Examples of protic solvents useful in the present invention include water, carboxylic acids, phenolic compounds, aliphatic alcohols and mixtures thereof. Specific examples of the protic solvents useful in the present invention include water, acetic acid, phenol, methanol, 2,3-dichloropropanol, and mixtures thereof. The protic solvent is preferably water or an aliphatic alcohol. The alcohol preferably contains about 1 to about 12 carbon atoms, more preferably contains about 1 to about 6 carbon atoms and most highly preferably contains about 1 to about 3 carbon atoms. Examples of suitable alcohols useful in the present invention include methanol, ethanol, propanol and 2,3-dihalopropanol such as 2,3-dichloropropanol.

Without intending to be bound to a particular theory, it is theorized that the protic solvent activates the catalyst, and stabilizes 2,3-dihalopropanal by formation of an equilibrium concentration of hydrate or hemiacetal. Generally, the amount of protic solvent which can be present in the reaction mixture of the present invention is from about 0 to about 99.99 weight percent, and preferably from about 5 to about 99.99 weight percent. However, alcohols, used as the protic solvent, also participate in certain competing side reactions in the presence of an acid. Therefore, it is preferable to either: (a) minimize the concentration of protic solvent to the lowest level at which the hydrogenation will run with a desired rate, or (b) run the reaction in the presence of an acid scavenger.

As one illustration of the present invention, the molar ratio of alcohol to dichloropropanal is preferably at least about 0.9:1 and no more than about 200:1. The optimum ratio within this range varies depending upon the presence or absence of an acid scavenger and the conditions of the reaction—such as temperature and pressure. For example, in one embodiment of the present process, a 2,3-dihalopropanal reacted with a stoichiometric quantity of molecular hydrogen in the presence of a ruthenium-containing catalyst and an alcohol, utilizes a molar ratio of alcohol to dichloropropanal of no more than 5:1.

The reaction of the present invention is optionally, but preferably carried out in the presence of an aprotic solvent. The aprotic solvent may be used alone in the reaction mixture or in combination with the protic solvent discussed above. The aprotic solvent is preferably inert with respect to all of the reagents under the reaction conditions. The aprotic solvent may be selected such that: (1) it does not boil under reaction conditions; and (2) 2,3-dihalopropanol can be recovered from it by distillation or extraction. Examples of suitable aprotic solvents useful in the present invention include aromatic and aliphatic hydrocarbons, ethers, glymes, glycol ethers and mixtures thereof. Specific examples of the aprotic solvent useful in the present invention include toluene, cyclohexane, hexane, dioxane, diphenyl ether, diglyme, 1,2-dimethoxyethane and mixtures thereof. The quantity of aprotic solvent is not critical and is governed primarily by practical considerations, such as the ability to dissolve the catalyst and the efficiency of the reactor. Generally, the amount of the aprotic solvent present in the reaction mixture ranges from 0 to about 99.99 weight percent.

In most cases, the reaction mixture of the present invention preferably contains at least about 5 weight percent 2,3-dihalopropanal, more preferably at least about 10 weight percent and most preferably at least about 20 weight percent. The reaction can be neat (about 100 weight percent 2,3-dihalopropanal), but if a solvent is used, for example a protic, aprotic or combination thereof, the reaction mixture preferably contains no more than about 90 weight percent dihalopropanal and more preferably no more than about 80 weight percent dihalopropanal.

When the reaction mixture contains an alcohol, the reaction is preferably carried out under conditions which are substantially free of strong mineral acids such as hydrogen chloride, which may cause a reduction in selectivity and yields. Substantially free of strong mineral acids means that the concentration of such acids is low enough that the acids do not catalyze the formation of acetals from the 2,3-dihalopropanal and alcohol. For example, the level of acetal formed by the acid catalyzed reaction between 2,3-dihalopropanal and an alcohol in the reaction mixture may be generally less than about 50 weight percent, preferably less than about 20 weight percent and most preferably less than about 1 percent.

Without intending to be bound to a particular theory, it is theorized that a strong acid catalyzes the reaction of 2,3-dihalopropanal and alcohol to form an undesirable acetal. The reaction mixture frequently contains minor quantities of hydrogen halide, and so the reaction is preferably carried out in the presence of an acid scavenger if alcohol is present to prevent acetal formation. Examples of suitable acid scavengers useful in the present invention include alkali metal carbonates, alkali metal bicarbonates, epoxides and mixtures thereof. Specific examples of acid scavengers include sodium carbonate, sodium bicarbonate, ethylene oxide, propylene oxide, butylene oxide, epichlorohydrin and mixtures thereof. Epichlorohydrin is the preferred epoxide to serve as an acid scavenger.

The temperature of the reaction is not critical, provided that all of the reagents and catalyst are in intimate contact with each other. However, low temperatures require longer reaction times. The reaction temperature is preferably at least about $-10°$ C., more preferably at least about $20°$ C. and most preferably at least about $50°$ C. The reaction temperature is preferably less than about $250°$ C., more preferably no more than about $150°$ C. and most preferably no more than about $120°$ C. The reaction temperature is preferably from about 0C. to about $200°$ C. and more preferably from about $50°$ C. to about $120°$ C.

The reaction pressure is not critical as long as there is sufficient hydrogen to run the reaction in the reaction mixture. The pressure is preferably at least about 14 psia (97 kPa, 1 atmosphere) and more preferably at least about 50 psia (340 kPa, 3.4 atmospheres). The pressure is preferably no more than about 3,000 psia (21 MPa, 220 atmospheres). Higher pressures could lead to shorter reaction times.

The product of the reaction of the present invention is a 2,3-dihalopropanol with a structure derived from the 2,3-dihalopropanal. The product may be recovered by known methods, such as extraction or distillation. The product may be recovered in yields as low as 2 percent, however, for economical purposes the product of the present invention is generally recovered in at least about 60 percent yields (based upon the initial quantity of 2,3-dihalopropanal), and preferably recovered in at least about 80 percent yields, more preferably in at least about 90 percent yields and most preferably in at least about 95 percent yields.

The reaction of the present invention is particularly useful in a process for making epichlorohydrin. Once the 2,3-dihalopropanol is made using the reaction of the present invention, the 2,3-dihalopropanol may be cyclized to make epihalohydrin by processes well-known in the art. More particularly, the reaction step of the present invention may be used in a four-step process to make epichlorohydrin from propylene as follows:

In Step (1), a 3-carbon hydrocarbon such as propylene is oxidized to form acrolein. Processes for this reaction are already well-known in the art and are described in the following references, which are incorporated herein by reference: Watanabe et al. (U.S. Pat. No. 4,008,281 (Feb. 15, 1977)); Childress et al. (U.S. Pat. No. 4,049,577 (Sep. 20, 1977)); Childress et al. (U.S. Pat. No. 4,129,600 (Dec. 12, 1978)); Daumas et al. (U.S. Pat. No. 4,166,808 (Sep. 4, 1979)); Caillod et al. (U.S. Pat. No. 5,225,389 (Jul. 6, 1993)) and Kobayashi et al. (U.S. Pat. No. 5,326,916 (Jul. 5, 1994)). In most cases, propylene is contacted in a gaseous phase with oxygen in the presence of a catalyst such as bismuth-phosphorous-molybdenum. Acrolein can also be made by oxidation of allyl alcohol. Acrolein is also commercially available, for example, from Aldrich Chemical Company, Inc. and Fisher Scientific Acros Organics.

In Step (2), acrolein is halogenated to make 2,3-dihalopropanal. This step has been described in U.S. Pat. No. 2,860,146, which is incorporated herein by reference. Preferably, the acrolein is contacted with molecular halogen, which is preferably molecular chlorine or molecular bromine and is more preferably molecular chlorine. The reaction temperature of Step (2) is preferably no more than about 125° C. and more preferably no more than about 50° C. It is preferably at least about −10° C. and more preferably at least about 0° C. The reaction of Step (2) can be run neat, or can take place in the presence of an organic solvent which is substantially inert with respect to all reagents under reaction conditions. Examples of suitable solvents useful in Step (2) include halogenated hydrocarbons, such as methylene chloride, 1,2-dichloroethane and 1,2-dichloropropane; dioxane; aliphatic hydrocarbons such as pentane, hexane, heptane; and mixtures thereof.

The concentration of water in the reaction mixture of Step (2) is preferably minimized because water reacts with the 2,3-dihalopropanal product to form impurities. This is particularly true when Step (3) is run in the presence of an alcohol, because water reacts with, for example chlorine to form hydrogen chloride which can catalyze acetal formation. When Step (3) uses alcohol, the concentration of water (as a percentage of acrolein) in Step (2) is preferably no more than about 2 weight percent, more preferably no more than about 1 weight percent and most preferably no more than about 0.5 weight percent. Although ideally the minimum concentration of water in Step (2) is 0 percent, about 0.1 weight percent may be more practical. Water can be excluded by known processes, such as by freeze drying, by use of molecular sieves and/or by adding dehydrating agents. The halogen, for example chlorine, partial pressure is preferably at a value which is balanced by the reactor heat removal rate. For example, the halogen partial pressure may be from about 0 (0 kPa) to about 30 psia (207 kPa). The yield of 2,3-dihalopropanal is preferably at least about 90 percent.

Step (3) is the reduction of 2,3-dihalopropanal to 2,3-dihalopropanol. The preferred embodiments of this step have been described previously in this application.

For example, one embodiment of the process of the present invention comprises the step of contacting a 2,3-dihalopropanal with at least a stoichiometric quantity of molecular hydrogen in the presence of a ruthenium-containing or iridium-containing catalyst and a protic solvent such as an alcohol, and, optionally, wherein the mixture further contains an acid scavenger.

Another embodiment of the process of the present invention comprises the step of contacting a 2,3-dihalopropanal with at least a stoichiometric quantity of hydrogen in the presence of a ruthenium-containing or iridium-containing catalyst and an aprotic solvent, wherein the mixture may optionally contain a protic solvent and/or an acid scavenger.

Step (4) is the conversion of 2,3-dihalopropanol to epihalohydrin. This step is well-known in the art of manufacturing epihalohydrin. The reaction of Step (4) is usually carried out by contacting the dihalopropanol with a strong base, such as an aqueous alkyl metal hydroxide, including for example sodium hydroxide. Examples of the Step (4) reaction are described in U.S. Pat. No. 2,860,146 and Wernli et al. (Australian Patent 630,238 (Feb. 12, 1993)), which are incorporated herein by reference.

Processes which use the present invention may contain any one or more of Steps (1), (2) and (4), in addition to Step (3). They preferably contain Steps (2) and (3), more preferably contain Steps (2), (3) and (4) and most preferably contain Steps (1)–(4).

The following examples are for illustrative purposes only and should not be taken as limiting the scope of either the Specification or the claims. Unless otherwise stated, all parts and percentages are by weight.

EXAMPLE 1

A solution containing 148 g of acrolein and 500 mL of methylene chloride was cooled to about 0° C. Chlorine was passed through the solution at atmospheric pressure with stirring and cooling to maintain the reaction mixture at below 18° C., until a slight yellow color of chlorine was observed to persist. The methylene chloride was distilled under reduced pressure to yield 253 g of 2,3-dichloropropanal, which was characterized by NMR.

A 300-mL Parr bomb reactor equipped with a mechanical stirrer was loaded with: 5 g of 2,3-dichloropropanal, 100 mL of ethanol and 200 mg of tris(triphenylphosphine)ruthenium (II) chloride. The reactor was sealed and pressurized with about 250 psig (1.7 mPa) hydrogen. The reactor was heated to 85° C. for three hours. The reactor was cooled and unreacted hydrogen was released. Ethanol was removed by distillation and the remaining liquid was treated with 150 mL of 5 percent ethyl acetate in hexane to form a solution. The solution was filtered through silica gel and then the hexane and ethyl acetate were removed by distillation to yield 3.5 g (70 percent) of 2,3-dichloro-1-propanol.

EXAMPLES 2–5

A quantity of 2,3-dichloropropanal, shown in Table I, was added slowly to one or more of the following: methanol, 1-cyclohexyl-2-pyrrolidinone, dioxane or water in the quantities shown in Table I. The 2,3-dichloropropanal was added slowly to minimize the exotherm observed in Examples 2–4. The mixture was sparge degassed with nitrogen and transferred to a 300 mL Parr reactor which had been charged with a ruthenium catalyst (Table I) and a nitrogen atmosphere. The reactor was pressurized with hydrogen, vented and then repressurized with hydrogen to about 1,000 psig (about 7 MPa) pressure. The reactor was heated to 85° C. for three hours. The reactor was cooled and unreacted hydrogen was vented.

In Example 2, methanol was removed by rotary-evaporation and the remaining liquids were distilled under reduced pressure to yield the quantity of 2,3-dichloropropanol product shown in Table I.

In Examples 3–5, the reaction mixture was analyzed by gas chromatographic (GC) analysis using decane as an internal standard and contained the quantity of 2,3-dichloropropanol product shown in Table I.

TABLE I

| Example | 2 | 3 | 4 | 5 |
|---|---|---|---|---|
| 2,3-dichloropropanal (g) | 50 | 5 | 5 | 1.3 |
| Catalyst | | | | |
| tris (triphenylphosphine) ruthenium (11) dichloride (g) | 2 | 0.2 | 0.2 | — |
| 5% ruthenium on carbon (g) | — | — | — | 5.44 |
| Solvents | | | | |
| 1-cyclohexyl-2-pyrrolidinone (g) | 10 | — | — | — |
| methanol (mL) | 50 | 100 | — | — |
| water (mL) | — | — | 2 | 0.8 |
| dioxane (mL) | — | — | 80 | 50.9 |
| Product | | | | |
| 2,3-dichloropropanol (percent yield) | 91% (46.1 g) | 96% | 94% | 83% |

General Procedure

The following general procedure was used in Examples 6–16:

A 300-mL Parr reactor was loaded with a catalyst charge (2,3-dichloropropanal (DCP):metal atom=100 to 200:1 for homogeneous catalysts and 10 to 50:1 for heterogeneous catalysts) and the reactor vessel was evacuated and nitrogen flushed three times. The solvent/DCP mixture was sparge degassed with nitrogen and added to the Parr reactor with a syringe. The reactor was pressurized/vented to 250/20 psig (1.7 mPa/138 kPa) nitrogen and 1000/20 psig (6.9 mPa/138 kPa) hydrogen, then placed under 1000 psig (6.9 mPa) hydrogen and heated to 65° C. to 100° C. Samples were removed by syringe after venting the reactor to less than 15 psig (103 kPa) or by using a valved dip tube.

Samples were analyzed by gas chromatography (GC) using a Hewlett Packard HP-5890 gas chromatograph equipped with a 25 m HP-5 Ultra 2 capillary column with split injection. Approximately 120 μL of the reaction mixture was dissolved in 5.0 mL of chloroform which contained a known amount of chlorobenzene as a GC standard (typically 0.05 weight percent). Selectivity is defined as the molar ratio of the amount of 2,3-dihalopropanol formed to the amount of 2,3-dihalopropanal consumed.

Air sensitive homogeneous catalyst precursors and activated heterogeneous catalysts were handled in an inert atmosphere glove box.

EXAMPLE 6

A 5.13 g (39.6 mmol) sample of 2,3-dichloropropanal was dissolved in a mixture of methanol (33.7 g) and toluene (33.2 g) and then added to RhCl (PPh$_3$)$_3$ (0.370 g; 0.40 mmol). The reactor was heated to 75° C. The reaction was sampled at 180 minutes with the following results:

| | GC Analysis | |
|---|---|---|
| Time (minutes) | Percent (%) Conversion | Percent (%) Selectivity |
| 180 | 22 | 85 |

EXAMPLE 7

A 2.21 g (17.4 mmol) sample of 2,3-dichloropropanal was dissolved in a mixture of dioxane (49.25 g) and water (1.72 g) and then added to 5 percent Rh on carbon (2.33 g; 1.1 mmol as Rh). The reactor was heated to 85° C. The reaction was sampled at 180 minutes with the following results:

| | GC Analysis | |
|---|---|---|
| Time (minutes) | % Conversion | % Selectivity |
| 180 | 93 | 13 |

EXAMPLE 8

A 5.00 g (39.28 mmol) sample of 2,3-dichloropropanal was dissolved in chloroform (141.41 g) and then added to (COD)Ir(PPh$_2$Me)$_2$$^+$PF$_6$$^-$ (0.3795 g; 0.449 mmol). The reactor was heated to 70° C. Samples were taken at times 0, 32 and 175 minutes with the following results:

| | GC Analysis | |
|---|---|---|
| Time (minutes) | % Conversion | % Selectivity |
| 0 | 0 | 0 |
| 32 | 31.7 | >98 |
| 175 | 50.8 | >98 |

EXAMPLE 9

A 4.00 g (31.5 mmol) sample of 2,3-dichloropropanal was dissolved in dioxane (48.76 g) and then added to 5 percent Ir on carbon (15.25 g; 4 mmol as Ir). The reactor was heated to 85° C. The reaction was sampled at 180 minutes with the following results:

| | GC Analysis | |
|---|---|---|
| Time (minutes) | % Conversion | % Selectivity |
| 180 | 100 | 74 |

EXAMPLE 10

A 5.13 g (40.40 mmol) sample of 2,3-dichloropropanal as dissolved in methanol (approximately 100 mL; 84.10 g) and then added to 5 percent Pt on silica (1.611 g; 0.4129 mmol as Pt). The reactor was heated to 70° C. Samples were taken at times 0, 31 and 173 minutes with the following results:

| | GC Analysis | |
|---|---|---|
| Time (minutes) | % Conversion | % Selectivity |
| 0 | 0 | 0 |
| 31 | 57.7 | 44.7 |
| 173 | 89.0 | 26.7 |

EXAMPLE 11

A 5.13 g (40.4 mmol) sample of 2,3-dichloropropanal was dissolved in methanol (74.09 g) and then added to 10 percent Pd on carbon (1.0 g, 0.94 mmol as Pd). The reaction was heated to 75° C. The reaction was sampled at 180 minutes with the following results:

| GC Analysis | | |
|---|---|---|
| Time (minutes) | % Conversion | % Selectivity |
| 180 | 100 | 2 |

EXAMPLE 12

A 2.72 g (21.4 mmol) sample of 2,3-dichloropropanal was dissolved in dioxane (55.98 g) and then added to 2 percent Ru on carbon (5.04 g, 1.0 mmol as Ru). The reactor was heated to 85° C. The reaction was sampled at 30, 60 and 180 minutes with the following results:

| GC Analysis | | |
|---|---|---|
| Time (minutes) | % Conversion | % Selectivity |
| 30 | 49 | 81 |
| 60 | 80 | 71 |
| 180 | 100 | 61 |

EXAMPLE 13

A 2.58 g (20.3 mmol) sample of 2,3-dichloropropanal was dissolved in dioxane (55.57 g) and then added to 5 percent Ru on silica (5.00 g; 1.2 mmol as Ru). The reactor was heated to 85° C. The reaction was sampled at 30, 90 and 180 minutes with the following results:

| GC Analysis | | |
|---|---|---|
| Time (minutes) | % Conversion | % Selectivity |
| 30 | 67 | 87 |
| 90 | 95 | 84 |
| 100 | 100 | 82 |

EXAMPLE 14

A 2.93 g (23.1 mmol) sample of 2,3-dichloropropanal was dissolved in dioxane (53.65 g) and then added to 2.5 percent Ir on silica (5.00 g; 0.7 mmol as Ir). The reactor was heated to 85° C. The reaction was sampled at 15 minutes with the following results:

| GC Analysis | | |
|---|---|---|
| Time (m) | % Conversion | % Selectivity |
| 15 | >95 | >95 |

EXAMPLE 15

A 2.62 g (20.6 mmol) sample of 2,3-dichloropropanal was dissolved in dioxane (51.35 g) and then added to 2.5 percent Ir on zirconia (1.05 g; 0.14 mmol as Ir). The reactor was heated to 85° C. The reaction was sampled at 30, 60 and 120 minutes with the following results:

| GC Analysis | | |
|---|---|---|
| Time (minutes) | % Conversion | % Selectivity |
| 30 | 63 | 100 |
| 60 | 76 | 100 |
| 120 | 89 | 94 |

EXAMPLE 16

A 2.56 g (20.1 mmol) sample of 2,3-dichloropropanal was dissolved in dioxane (50.69 g) and then added to 0.25 percent Ir on alumina (5.01 g; 0.06 mmol as Ir). The reactor was heated to 85° C. The reaction was sampled at 30, 60 and 180 minutes with the following results:

| GC Analysis | | |
|---|---|---|
| Time (minutes) | % Conversion | % Selectivity |
| 30 | 26 | 86 |
| 60 | 31 | 79 |
| 120 | 38 | 75 |

What is claimed is:

1. A process to make 2,3-dihalopropanol or 2,3-dihalo-2-alkylpropanol comprising the step of reacting 2,3-dihalopropanal or 2,3-dihalo-2-alkylpropanol with molecular hydrogen in the presence of a transition metal-containing catalyst selected from the group comprising iron, cobalt, nickel, ruthenium, rhodium, palladium, osmium, iridium, platinum and mixtures thereof, under conditions such that 2,3-dihalopropanol or 2,3-dihalo-2-alkylpropanol is formed.

2. The process described in claim 1 wherein the 2,3-dihalopropanal is selected from the group comprising 2,3-dichloropropanal; 2,3-dibromopropanal; 2,3-dichloro-2-methylpropanal and 2,3-dibromo-2-methylpropanal.

3. The process described in claim 1 wherein the 2,3-dihalopropanal is unsubstituted 2,3-dichloropropanal and the 2,3-dihalopropanol formed is 2,3-dichloropropanol.

4. The process described in claim 1 wherein the 2,3-dihalopropanal is unsubstituted 2,3-dibromopropanal and the 2,3-dihalopropanol formed is 2,3-dibromopropanol.

5. The process described in claim 1 wherein the ratio of molecular hydrogen to dihalopropanal is at least about 0.75:1.

6. The process described in claim 5 wherein the ratio of molecular hydrogen to dihalopropanal is at least about 0.6:1.

7. A process to make 2,3-dihlopropanol or 2,3-dihalo-2-alkylpropanol comprising the step of reacting 2,3-dihalopropanal or 2,3-dihalo-2-alkylpropanol with molecular hydrogen in the presence of a homogeneous transition metal-containing catalyst, under conditions such that 2,3-dihalopropanol or 2,3-dihalo-2-alkylpropanol is formed.

8. A process to make 2,3-dihalopropanol or 2,3-dihalo-2-alkylpropanol comprising the step of reacting 2,3-dihalopropanal or 2,3-dihalo-2-alkylpropanol with molecular hydrogen in the presence of a heterogeneous transition metal-containing catalyst, under conditions such that 2,3-dihalopropanol or 2,3-dihalo-2-alkylpropanol is formed.

9. The process as described in claim 1 wherein the catalyst contains a ruthenium compound or complex.

10. The process as described in claim 1 wherein the catalyst contains iridium.

11. The process as described in claim 10 wherein the catalyst contains an iridium compound or complex.

12. A process to make 2,3-dihalopropanol or 2,3-dihalo-2-alkylpropanol comprising the step of reacting 2,3-dihalopropanal or 2,3-dihalo-2-alkylpropanol with molecular hydrogen in the presence of a transition metal-containing catalyst under conditions such that 2,3-dihalopropanol or 2,3-dihalo-2-alkylpropanol is formed; wherein the catalyst further contains a coordinating ligand.

13. The process as described in claim 12 wherein the ligand is selected from the group comprising phosphines, 1,5-cyclooctadiene (COD), arsines, stibines, carbon monoxide, ethers, cyclopentadienyl, sulfoxides, and aromatic amines and mixtures thereof.

14. The process as described in claim 13 wherein the ligand is phosphine.

15. The process as described in claim 8 wherein the catalyst is a heterogeneous catalyst which contains a transition metal deposited upon a supporting material.

16. The process of claim 15 wherein the supporting material is selected from the group comprising carbon, silica, alumina, titania, zirconia and combinations thereof.

17. The process of claim 7 wherein the homogeneous catalyst is present in the reaction mixture at a concentration of at least about 0.01 mmoles of catalyst metal per mole of dihalopropanal.

18. The process of claim 8 wherein the heterogeneous catalyst is in the form of a heterogeneous catalyst bed in a reactor, and wherein the heterogeneous catalyst is present in the reaction mixture at a ratio of about 0.0001 to about 100 moles of catalyst metal for each mole of dihalopropanal which passes through the bed per hour.

19. The process as described in claim 1 wherein the catalyst is selected from the group comprising $RuCl_2(PPh_3)_3$, $RuH(CF_3CO_2)(PPh_3)_3$, $RuH(CH_3CO_2)(PPh_3)_3$, $RuHCl(PPh_3)_3$, $RuCl_2(PPh_2\text{-ptol})_3$, $RuHCl(CO)(PPh_3)_3$, $RuCl_2[P(C_6H_4\text{-m-}CH_3)_3]_3$, $RuCl_3/P(p\text{-tol})_3$, $RuCl_3/P(C_6H_4\text{-}p\text{-Cl})_3$, $\{RuCl_2[P(C_6H_4\text{-m-}SO_3Na)_3]_2\}_2$, $RuHCl(PPh_3)_2$(NBD), $RuH_2(PPh_3)_4$, polystyrene supported $RuCl_2(PPh_3)_3$, $RuHCl(dppe)_2$, $RhCl(PPh_3)_3$, $(COD)Ir(PPh_2Me)_2^+ PF_6^-$, Ru on carbon, Ru on alumina, Ru on silica, Ir on carbon, Ir on alumina, and Ir on silica, Rh on carbon, Rh on silica, Rh on alumina, Pt on carbon, Pt on silica, Pt on alumina, Pd on carbon, Pd on silica, Pd on alumina, and mixtures thereof.

20. The process as described in claim 19 wherein the catalyst is $RuCl_2(PPh_3)_3$.

21. The process as described in claim 19 wherein the catalyst is selected from the group comprising Ru on carbon, Ru on alumina, Ru on silica and mixtures thereof.

22. The process as described in claim 19 wherein the catalyst is selected from the group comprising Ir on carbon, Ir on alumina, Ir on silica, and mixtures thereof.

23. The process as described in claim 1 which is carried out with a hydrogen partial pressure of at least about 14 psia.

24. A process to make 2,3-dihalopropanol or 2,3-dihalo-2-alkylpropanol comprising the step of reacting 2,3-dihalopropanal or 2,3-dihalo-2-alkylpropanol with molecular hydrogen in the presence of a transition metal-containing catalyst under conditions such that 2,3-dihalopropanol or 2,3-dihalo-2-alkylpropanol is formed; wherein the reaction mixture further contains a protic solvent.

25. The process as described in claim 24 wherein the protic solvent is selected from the group comprising water, carboxylic acids, phenolic compounds, aliphatic alcohols or mixtures thereof.

26. The process as described in claim 25 wherein the protic solvent is water.

27. The process as described in claim 25 wherein the protic solvent is an aliphatic alcohol.

28. The process as described in claim 27 wherein the reaction mixture contains an aliphatic alcohol which contains 1 to 12 carbon atoms.

29. The process as described in claim 25 wherein the protic solvent is 2,3-dihalopropanol.

30. The process as described in claim 29 wherein the protic solvent is present in the reaction mixture at from about 0 to 99.99 weight percent.

31. A process to make 2,3-dihalopropanol or 2,3-dihalo-2-alkylpropanol comprising the step of reacting 2,3-dihalopropanal or 2,3-dihalo-2-alkylpropanol with molecular hydrogen in the presence of a transition metal-containing catalyst under conditions such that 2,3-dihalopropanol or 2,3-dihalo-2-alkylpropanol is formed; wherein the reaction mixture further contains an aprotic solvent.

32. The process as described in claim 31 wherein the aprotic solvent is selected from the group comprising aromatic hydrocarbons, aliphatic hydrocarbons, ethers, glymes, glycol ethers, and mixtures thereof.

33. The process as described in claim 32 wherein the aprotic solvent is an aliphatic hydrocarbon.

34. The process as described in claim 32 wherein the aprotic solvent is present in the reaction mixture of from 0 to about 99.99 weight percent.

35. A process to make 2,3-dihalopropanol or 2,3-dihalo-2-alkylpropanol comprising the step of reacting 2,3-dihalopropanal or 2,3-dihalo-2-alkylpropanol with molecular hydrogen in the presence of a transition metal-containing catalyst under conditions such that 2,3-dihalopropanol or 2,3-dihalo-2-alkylpropanol is formed; wherein the reaction mixture further contains an acid scavenger.

36. The process as described in claim 35 wherein the acid scavenger is selected from the group comprising alkali metal carbonates, alkali metal bicarbonate, epoxides and mixtures thereof.

37. The process as described in claim 36 wherein the acid scavenger is epichlorohydrin.

38. The process as described in claim 1 comprising the step of contacting a 2,3-dihalopropanal with at least a stoichiometric quantity of molecular hydrogen in the presence of a ruthenium-containing catalyst or an iridium-containing catalyst and a protic solvent.

39. The process as described in claim 38 wherein the protic solvent is an alcohol.

40. The process as described in claim 38 wherein the mixture further contains an acid scavenger.

41. The process as described in claim 1 comprising the step of contacting a 2,3-dihalopropanal with at least a stoichiometric quantity of hydrogen in the presence of a ruthenium-containing catalyst or an iridium-containing catalyst and an aprotic solvent.

42. The process as described in claim 41 wherein the mixture further contains a protic solvent.

43. The process as described in claim 41 wherein the mixture further contains an acid scavenger.

44. The process as described in claim 42 wherein the mixture further contains an acid scavenger.

45. The process as described in claim 42 wherein the protic solvent is water.

46. A process to make epihalohydrin comprising the steps of:
   (a) reducing 2,3-dihalopropanal as described in claim 1 to form 2,3-dihalopropanol; and
   (b) contacting the 2,3-dihalopropanol with a base, whereby an epihalohydrin is formed.

47. A process to make epihalohydrin comprising the steps of:

(a) halogenating acrolein to make 2,3-dihalopropanal;

(b) reducing 2,3-dihalopropanal as described in claim 1 to form 2,3-dihalopropanol; and (c) contacting the 2,3-dihalopropanol with a base, whereby an epihalohydrin is formed.

48. A process to make epihalohydrin comprising the steps of:

(a) reacting a hydrocarbon which contains 3 carbon atoms with an oxidizing agent to form acrolein;

(b) reacting acrolein with a molecular halogen to form 2,3-dihalopropanal;

(c) reducing 2,3-dihalopropanal to form 2,3-dihalopropanol as described in claim 1 to form 2,3-dihalopropanol; and (d) contacting the 2,3-dihalopropanol with a base, whereby an epihalohydrin is formed.

\* \* \* \* \*

UNITED STATES PATENT AND TRADEMARK OFFICE
CERTIFICATE OF CORRECTION

PATENT NO : 6,008,419

DATED : December 28, 1999

INVENTOR(S) : P.J. Thomas, R. Garth Pews, Paul C. Vosejpka, George J. Frycek

It is certified that error appears in the above-identified patent and that said Letters Patent is hereby corrected as shown below:

Claim 1, line 3, "2,3-dihalo-2-alkylpropanol" should read --2,3-dihalo-2-alkylpropanal--.

Claim 7, line 3, "2,3-dihalo-2-alkylpropanol" should read --2,3-dihalo-2-alkylpropanal--.

Claim 8, line 3, "2,3-dihalo-2-alkylpropanol" should read --2,3-dihalo-2-alkylpropanal--.

Claim 12, line 3, "2,3-dihalo-2-alkylpropanol" should read --2,3-dihalo-2-alkylpropanal--.

Claim 24, line 3, "2,3-dihalo-2-alkylpropanol" should read --2,3-dihalo-2-alkylpropanal--.

Claim 31, line 3, "2,3-dihalo-2-alkylpropanol" should read --2,3-dihalo-2-alkylpropanal--.

Claim 35, line 3, "2,3-dihalo-2-alkylpropanol" should read --2,3-dihalo-2-alkylpropanal--.

Signed and Sealed this

Twenty-seventh Day of February, 2001

Attest:

NICHOLAS P. GODICI

Attesting Officer

Acting Director of the United States Patent and Trademark Office